(12) United States Patent
Nörenberg et al.

(10) Patent No.: US 6,627,455 B1
(45) Date of Patent: Sep. 30, 2003

(54) USE OF FLUORESCENT DYES FOR SURFACE ANALYSIS

(75) Inventors: Ralf Nörenberg, Chemnitz (DE); Wolfgang Schrof, Neuleiningen (DE); Norbert Mahr, Limburgerhof (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,585

(22) PCT Filed: Feb. 13, 1999

(86) PCT No.: PCT/EP99/00953

§ 371 (c)(1),
(2), (4) Date: Aug. 21, 2000

(87) PCT Pub. No.: WO99/42812

PCT Pub. Date: Aug. 26, 1999

(30) Foreign Application Priority Data

Feb. 21, 1998 (DE) .......................................... 198 07 405

(51) Int. Cl.$^7$ ............................................. G01N 21/76
(52) U.S. Cl. .......................... 436/172; 436/86; 436/89; 436/106; 436/111
(58) Field of Search ........................... 436/172, 86, 89, 436/106, 111

(56) References Cited

U.S. PATENT DOCUMENTS 5,442,045 A * 8/1995 Haugland et al. ........ 530/391.3

FOREIGN PATENT DOCUMENTS

EP 0 455 905 11/1991

OTHER PUBLICATIONS

A. J. G. Mank, et al., Analytical Chenistry, vol. 67, No. 10, pp. 1742 to 1748, "Visible Diode Laser–Induced Fluorescence Detection in Liquid Chromatography After Precolumn Derivatization of Amines", May 15, 1995.

H, Fujino, et al., Analytical Sciences, vol. 6, pp. 465–466, "7–Methoxycoumarin–3–Carbonyl Fluoride as a Fluorescent Labeling Reagent for Primary Amines in High Performance Liquid Chromatography", Jun. 1990.

H. Nakamura, et al., Journal of Chromatography, vol. 200, pp. 324 to 329, "Fluorescence Detection of Secondary Amines on Thin–Layer Plates Using a Fluorogenic Reaction with Fluorescamine", 1980.

* cited by examiner

*Primary Examiner*—Jill Warden
*Assistant Examiner*—Monique T. Cole
(74) *Attorney, Agent, or Firm*—Oblon, Spivak, McClelland, Maier & Neustadt, P.C.

(57) ABSTRACT

Fluorescent dyes bearing at least one reactive group capable of reaction with nucleophilic groups are used for the qualitative and, if desired, quantitative fluorescence-analytical determination of the surface adsorption of compounds bearing amino and/or imino groups.

35 Claims, No Drawings

USE OF FLUORESCENT DYES FOR SURFACE ANALYSIS

DESCRIPTION

The present invention relates to the use of fluorescent dyes bearing at least one reactive group capable of reaction with nucleophilic groups for the qualitative and, if desired, quantitative fluorescence-analytical determination of the surface adsorption of compounds bearing amino and/or imino groups.

The most common use for fluorescent dyes is in dyeing/coloring fibers and moldings. However, the property of fluorescence is also utilized in analysis. For instance, fluorescent chromophores are used in biochemistry for labeling antibodies or low molecular weight compounds in immunoassays or other immunological methods of detection. However, in these methods, the fluorescent dyes are coupled to the detecting reagents prior to the detection reaction.

One method for analyzing amine mixtures is described in Anal. Chem. 1995, 67, 1742–1748. Here, amine mixtures are labeled with fluorescent dyes containing a succinimidyl ester radical and separated by liquid chromatography, and the qualitative and quantitative composition of the mixture is determined against previously prepared reference samples.

The determination of the adsorption of amines on surfaces has a different purpose. It is concerned not with the detection of certain amines in mixtures, but with the affinity of an oligo- or polyamine for certain materials.

To develop textile, leather and paper assistants, it is very important to know the degree of adsorption of the oligo- or polyamine when used on the substrates. Examinations into the affinity of specific oligo- and polyamines for the substrates are particularly important when used with other kinds of assistants.

It is an object of the present invention to provide labels providing qualitative and, if desired, quantitative information on oligo- and/or polyamines adsorbed on the substrate.

We have found that this object is achieved by the use of fluorescent dyes bearing at least one reactive group capable of reaction with nucleophilic groups for the qualitative and quantitative fluorescence-analytical determination of the surface adsorption of compounds bearing amino and/or imino groups.

In useful fluorescent dyes, the chemical nature of the chromophore matters only to a minor degree. What is essential, on the contrary, is its reactive group, which forms a rapid bond with any adsorbed compounds having amino and/or imino groups. Fluorescent dyes are known to those skilled in the art and are described for example in Ullmann's Encyclopedia of Industrial Chemistry 5$^{th}$ Ed., Vol. A11, p. 279. Useful classes of such dyes are naphthalimides, coumarins, xanthenes, thioxanthenes, naphthilactams, azlactones, methines, stilbenes, oxazines and thiazines.

Particularly good fluorescent dyes in commercial practice are coumarins such as derivatives of 7-dialkylaminocumarin, xanthenes such as fluorescein and its halogenation products eosine, erythrosine, phloxine and Rose bengal and rhodamines and in particular methine dyes such as cyanines.

For the fluorescence-analytical examination of surfaces on which other fluorescent compounds are adsorbed, the dye chosen will differ significantly in its fluorescence spectrum from those of the other adsorbed compounds. In the case of optical brighteners as used in paper, for example, the dye chosen would fluoresce in the red or near infrared region of the spectrum.

The reactive groups, of which at least one is attached to the chromophore, usefully include radicals which react with the nucleophilic amino or imino group, for example Michael systems, such as vinylsulfonyl or the acid sulfuric esters which form these under basic conditions by elimination. Also useful are reactive groups known from peptide chemistry, such as acetyl azide, aryl halide, dichlorotriazine, isothiocyanate, sulfonyl chloride and sulfosuccinimidyl ester radicals. For cases where the substrates have adsorbed a plurality of nucleophilically reacting compounds capable of competing with the amino and imino groups, the dyes used would have reactive radicals which are selective with regard to amino and imino groups.

Particularly useful in these cases are succinimidyl esters combining high selectivity with good stability in aqueous solutions.

It is possible in this connection to use such fluorescent dyes as are commercially available as labeling agents for biomolecules such as proteins and antibodies directly for dyeing. Examples of common commercial labeling agents are cyanines containing one or more succinimidyl ester radicals.

Succinimidyl esters are incidentally also preparable simply by reacting fluorescent dyes bearing carboxyl groups with N-hydroxysulfosuccinimides.

The surface is examined by applying a dye solution to a sample of the substrate to be examined. In those areas of the surface where compounds bearing amino or imino groups are adsorbed, the dye becomes attached. A subsequent rinsing step washes away unattached dye. This enables fluorescence microscopy to be used to obtain an image of the coverage of the surface.

Compounds having amino and/or imino groups that are advantageously determinable by dyeing with fluorescent dyes are oligo- and polyamines bearing amino or imino groups. The amino or imino groups are attached to aliphatic or aromatic chains and may contain further functional radicals or else quaternary ammonium ions as well as the amino groups. Such compounds are used as assistants in various applications.

Examples are polyvinylamines as described for example in U.S. Pat. No. 4,217,214, EP-A-071 050 and EP-A-0 216 387. These compounds are polymers of N-vinylcarboxamides or their copolymers with ethylenically unsaturated monomers that are converted into polyvinylamines after the polymerization by elimination of the carboxylic acid radicals. Such polyvinylamines are used for example as paper assistants for fixating water-soluble and -insoluble contraries and have average molecular weights $M_w$ of from 200 to 10 million.

Similarly readily dyeable oligo- and polyamines are polyethyleneimines as described in U.S. Pas. No. 2,182,306 or U.S. Pat. No. 3,203,910, which have average molecular weights $M_w$ of from 250 to 2 million, usually from 500 to 10,000, when used as assistants in various applications. An example is the use of polyethyleneimines as retention aids in papermaking.

It will be appreciated that derivatives of polyvinylamines and polyethyleneimines are similarly readily dyeable, as long as not all free amino groups have been derivatized. Derivatizing reactions include for example carboxymethylations and also reactions with alkyl epoxides as described in WO-A-97/40087 and WO-A-97/42229.

Readily detectable amines further include oligoamines obtained by condensation reaction of, for example, primary mono- or diamines or secondary diamines with epichlorohydrin. Further examples include the addition products of these amines with acrylonitrile and subsequent hydrogenation. Examples of the first type of oligoamine mentioned are partially quaternized piperazine condensates with epichlorohydrin that have an average molecular weight of from 200 to 70,000. These amines are used as textile assistants in the dyeing of cotton fibers.

The use of fluorescent dyes permits the detection of compounds bearing amino and/or imino groups that are adsorbed on any surfaces of substrates.

Examples are paper, wood, leather, fabrics composed of manufactured or natural fibers, hairs, fur, sheet-silicate, hard surfaces such as glass, metal, ceramic or else catalyst surfaces.

The surfaces may have become coated with the oligo- or polyamines for example by treatment with decontaminating or cleaning formulations. However, they may also have become coated in the course of a finish operation on fibers and fabrics or directly during, for example, papermaking.

Such oligo- and polyamines have different molecular weights, depending on application requirements. However, this is immaterial to the dyeing of the oligo- and polyamines on the substrate, since they are adsorbed on the surface. The limit of detection is not reached until the amines to be assayed are so readily detached from the surface that this takes place during the brief dyeing and rinsing step.

The dyeing step is generally carried out using an aqueous solution of the fluorescent dye. Aqueous solution as used herein also encompasses solutions which, as well as water, contain up to 20% by weight of a water-miscible organic solvent such as $C_1$- to $C_4$-alkanols, especially methanol, ethanol, isopropanol or a cyclic ether such as tetrahydrofuran. Preferably, however, water is used as sole solvent. The pH of the solution should be in the range of 5–14, preferably from 6 to 10. Since more acidic conditions would cause a protonation of the amino groups, this would lead to a slowing down of the reaction. The pH can be set not only by means of an inorganic base such as the hydroxides, oxides and basic salts of alkali and alkaline earth metals, eg sodium hydroxide, potassium hydroxide, sodium carbonate, potassium carbonate or calcium carbonate, or using buffer systems.

Since fluorescence-spectroscopic analysis is very sensitive, it is not necessary to obtain an equimolar conversion of the amino or imino groups. On the contrary, it is sufficient to use only from 0.1 to $10^{-5}$ equivalents of fluorescent dye per one equivalent of free amino group.

The concentration of the dye may range from $10^{-3}$ to $10^{-6}$ Mol/l. If commercially available labeling dyes for biopolymers are used, these can be used in the same concentrations as predescribed for the labeling reaction.

The dyeing step is generally completed within a few minutes and is preferably carried out at room temperature.

The dyeings can be obtained not only by spraying but also by dipping a substrate sample into the dyeing solution.

After dyeing, the unbound dye is removed by rinsing with water or the aqueous solvent mixture.

Fluorescence-analytical determinations are generally carried out as fluorescence-microscopic examinations, preferably using reflected light microscopes. Single- or two-proton excitations, laser scanning means and a confocal setting may be used, for example. It is similarly possible to employ spectrally or time-resolved fluorescence detection in order that double labelings with different dyes may be examined.

Possible dyeability of the uncoated surface and attendant fluorescence and also possible self-fluorescence of the substrate is ascertainable through simple blank experiments and may readily be compensated for as background signals.

The observer sees a surface where the oligo- or polyamines appear as dots, so that he or she is able to identify locations of high density on a fabric, for example. This accordingly provides qualitative information on which parts and to what degree the surface is covered with amines. It is similarly possible to ascertain the depth to which the amines have penetrated by examining a cross section.

This dyeing method also provides quantitative information on the amount of amine adsorbed from a previously prepared calibration line. This is a simpler, faster method of examination than conventional methods in the product development of amines and in the production of new formulations using such amines.

The inventive use of fluorescent dyes further permits the parallel determination of the adsorption of a group of compounds bearing amino and/or imino groups on the surface to be examined and can be utilized for selecting amines having good adsorption characteristics.

This provides a simple way of testing various oligo- and polyamines concurrently by applying them in a defined amount to various areas of a sample surface and then staining the surface with fluorescent dyes. After the unbound dye has been removed, subsequent quantitative evaluation of the individual spots by means of fluorescence microscopy permits a comparison of the adsorption characteristics of the amines examined. The high sensitivity of fluorescence microscopy permits a miniaturized sample and hence the parallel examination of a large number of compounds with regard to their adsorption characteristics.

This labeling with fluorescent dyes further enables the adsorption characteristics of amines on sheet-silicates to be examined, which is very important for assessing the eliminability of amines in environmental analysis.

An important advantage of the use of fluorescent dyes is that it provides qualitative and quantitative information on adsorbed oligo- and polyamines without the adsorption process being affected by a modification effected prior to adsorption.

The examples hereinbelow illustrate the invention.

EXAMPLE 1

Amine detection on leather:

An ampoule of Cy5® (about 0.127 mg; from Amersham), a fluorescent dye of the formula

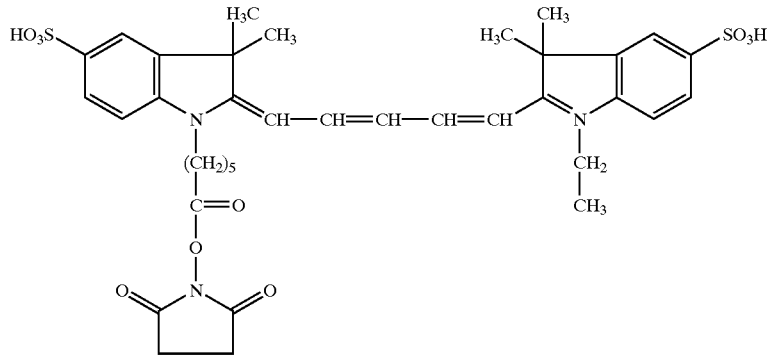

was dissolved in 200 ml of distilled water (solution 1).

Dyeing Prescription 1 ml of the fluorescent dye solution was applied to the leather. After 1 minute the substrate was introduced into a rinsing apparatus where it was subjected to a laminar stream of distilled water. The leather was rinsed for 5 min and then removed.

Sample Preparation a) Polyethyleneimine (molar mass about 10,000 g/mol) was dissolved in distilled water in a concentration of 10 g/l, applied to a piece of grain leather in a concentration of about 0.02 mg/g and rinsed off under running water (sample 1).
b) A second piece of grain leather was stained with the fluorescent dye as per the dyeing prescription without treatment with polyethyleneimine (sample 2).
c) A third piece of grain leather was treated with polyethyleneimine as described under a) and subsequently stained as per the dyeing prescription (sample 3).

Measurement and Analysis

All three samples were subjected to measurement of the intensity of fluorescence. The measurements were carried out in a fluorescence spectrometer (SPEX Fluorolog® II) after excitation at 620 nm. The fluorescence signals of sample 1 (self-fluorescence of polyethyleneimine) and of sample 2 (self-dyeability of leather) were detected from the signal of sample 3 to determine the coverage of the surface.

EXAMPLE 2

Amine Detection on Polyester Fabric

Sample Preparation a) A partially quaternized polypiperazine condensate (molar mass about 30,000 g/mol) was dissolved in distilled water in a concentration of 10 g/l, applied to a polyester fabric in various concentrations ranging from 0.01 to 0.05 mg of polypiperazine/g of fabric and rinsed off under running water. This was followed by staining by the dyeing prescription of Example 1 (sample 4).
b) A piece of polyester fabric was stained as described in Example 1 directly without treatment with the polypiperazine condensate (sample 5).
c) A piece of polyester fabric was treated with 0.05 mg of polypiperazine/g of fabric (sample 6). The sample did not show increased fluorescence.

The intensity of fluorescence of samples 4, 5 and 6 was determined. The measurements were carried out in a fluorescence spectrometer (SPEX Fluorolog® II) after excitation at 620 nm. Sample 5 was used to determine the self-fluorescence of the fabric, the baseline, which remained unchanged by unstained piperazine condensate (sample 6). The pieces of polyester fabric covered with different concentrations of polymin by the above method were then likewise examined fluorescence-optically. The adsorption of the piperazine condensate was detected as a fluorescence signal remaining after subtraction of the signals of samples 5 and 6. The intensity of fluorescence correlated with the offered amount of quaternized piperazine condensate in accordance with the adsorption isotherms.

EXAMPLE 3

Amine Detection on Bentonite (sheet silicate)

a) Dyeing Prescription
50 ml of a suspension containing about 6 g of bentonite (average particle size 200 nm) were centrifuged for 15 min at 15,000 rpm after adsorption. The centrifugate was slurried up in 50 ml of distilled water and again centrifuged for 15 min at 15,000 rpm. The centrifugate was again taken up in distilled water and admixed with 2 ml of the dye solution described in Example 1. The sample was centrifuged, slurried up in 50 ml of distilled water, centrifuged and applied to a microwell plate.

b) Treatment with Polyethyleneimine
150 ml of a suspension (solids content 2% by weight) were admixed with 20 ml of a polyethyleneimine solution (average molecular weight 10,000 g/mol) (10 g/l). After 20 min 50 ml of the suspension were centrifuged at 15,000 rpm and thereafter slurried up in water. The centrifuging and taking up in distilled water was repeated before the staining was carried out.

Sample Preparation and Measurement

A bentonite suspension was treated with polyethyleneimine as described under b) and stained as described under a). The intensity of fluorescence was measured (sample 7). The fluorescence was measured in a fluorescence spectrometer (SPEX Fluorolog II) after excitation at 620 nm.

A reference sample was prepared under identical conditions but without polyethyleneimine in step b) (sample 8). The intensity of fluorescence of this sample was likewise measured.

For evaluation, the signal for reference sample 8 was deducted from the signal for sample 7. The adsorption of polyethyleneimine on bentonite was detectable by a remaining signal of fluorescence.

We claim:

1. A method of determining the surface adsorption of one or more compounds, oligomers or polymers having amino and/or imino groups, comprising: applying a fluorescent dye having at least one group reactive with amino and/or imino groups to a surface having one or more adsorbed compounds, oligomers or polymers having amino and/or imino groups, determining the surface coverages of said one or more adsorbed compounds, oligomers or polymers, and correlating said surface coverages of reacted fluorescent dye to said surface adsorption of said one or more adsorbed compounds, oligomers or polymers.

2. The method of claim 1, wherein the reactive group is capable of selective reaction with amino groups.

3. The method of claim 1, wherein the reactive group is a succinimidyl ester.

4. The method of claim 1, wherein the reactive group is vinylsulfonyl, sulfuric esters, acetyl azide, aryl halide, dichlorotriazine, isothiocyanate, sulfonyl chloride, sulfosuccinimidyl esters or succinimidyl esters.

5. The method of claim 1, wherein said surface has one or more adsorbed compounds, oligomers or polymers having amino groups.

6. The method of claim 1, wherein said surface is a fabric.

7. The method of claim 1, wherein said surface is leather.

8. The method of claim 1, wherein said surface is bentonite.

9. The method of claim 1, wherein said surface is paper, wood, leather, fabric, hair, fir, bentonite, glass, metal, ceramic or catalyst.

10. The method of claim 1, wherein amines having good adsorption characteristics are selected by parallel determination.

11. The method of claim 1, wherein said surface has one or more adsorbed compounds, oligomers or polymers with imino groups having at least one group reactive with amino and/or imino groups to a surface having one or more oligomers or polymers with amino and/or imino groups.

12. The method of claim 1, wherein the surface has one or more oligomers or polymers with amino and/or imino group.

13. The method of claim 12, wherein the reactive group is capable of selective reaction with amino groups.

14. The method of claim 12, wherein the reactive group is a succinimidyl ester.

15. The method of claim 12, wherein the reactive group is vinylsulfonyl, sulfuric esters, acetyl azide, aryl halide, dichlorotriazine, isothiocyanate, sulfonyl chloride, sulfosuccinimidyl esters or succinimidyl esters.

16. The method of claim 12, wherein said surface has adsorbed oligo- and/or polyamines.

17. The method of claim 12, wherein said surface is a fabric.

18. The method of claim 12, wherein said surface is leather.

19. The method of claim 12, wherein said surface is bentonite.

20. The method of claim 12, wherein said surface is paper, wood, leather, fabric, hair, fur, bentonite, glass, metal, ceramic or catalyst.

21. The method of claim 13, wherein amines having good adsorption characteristics are selected by parallel determination.

22. The method of claim 12, wherein said surface has one or more oligomers or polymers with imino groups.

23. The method of claim 1, wherein said fluorescent dye is from 0.1 to $10^{-5}$ equivalents per one equivalent of amino and/or imino group.

24. The method of claim 1, wherein the concentration of said fluorescent dye ranges from $10^{-3}$ to $10^{-6}$ mol/l.

25. A method of determining the surface adsorption of one or more compounds, oligomers or polymers having amino and/or imino groups, comprising: applying a fluorescent dye having at least one group reactive with amino and/or imino groups to a surface having one or more adsorbed compounds, oligomers or polymers with amino and/or imino groups, determining the surface coverages of said one or more adsorbed compounds, oligomers, or polymers by fluorescence microscopy, and correlating said surface coverages of reacted fluorescent dye to said surface adsorption of said one or more adsorbed compounds, oligomers or polymers.

26. The method of claim 25, wherein said fluorescent dye is in aqueous solution with a pH of 5–14.

27. The method of claim 25, wherein said fluorescent dye is from 0.1 to $10^{-5}$ equivalents per one equivalent of amino and/or imino group.

28. The method of claim 25, wherein the concentration of said fluorescent dye ranges from $10^{-3}$ to $10^{-6}$ mol/l.

29. The method of claim 25, wherein the surface has one or more oligomers or polymers with amino and/or imino groups.

30. The method of claim 25, wherein said fluorescent dye is in aqueous solution with a pH of 5–14.

31. The method of claim 22, wherein sad surface has one or more adsorbed compounds, oligomers or polymers with amino groups.

32. The method of claim 25, wherein said surface has one or more adsorbed compounds, oligomers or polymers with imino groups.

33. The method of any one of claim 12 or 29, wherein said fluorescent dye is in aqueous solution with a pH of 5–14.

34. The method of any one of claim 12 or 29, wherein said fluorescent dye is from 0.1 to $10^{-5}$ equivalents per one equivalent of amino and/or imino group.

35. The method of any one of claim 12 or 29, wherein the concentration of said fluorescent dye ranges from $10^{-3}$ to $10^{-6}$ mol/l.

* * * * *